Figure 1:
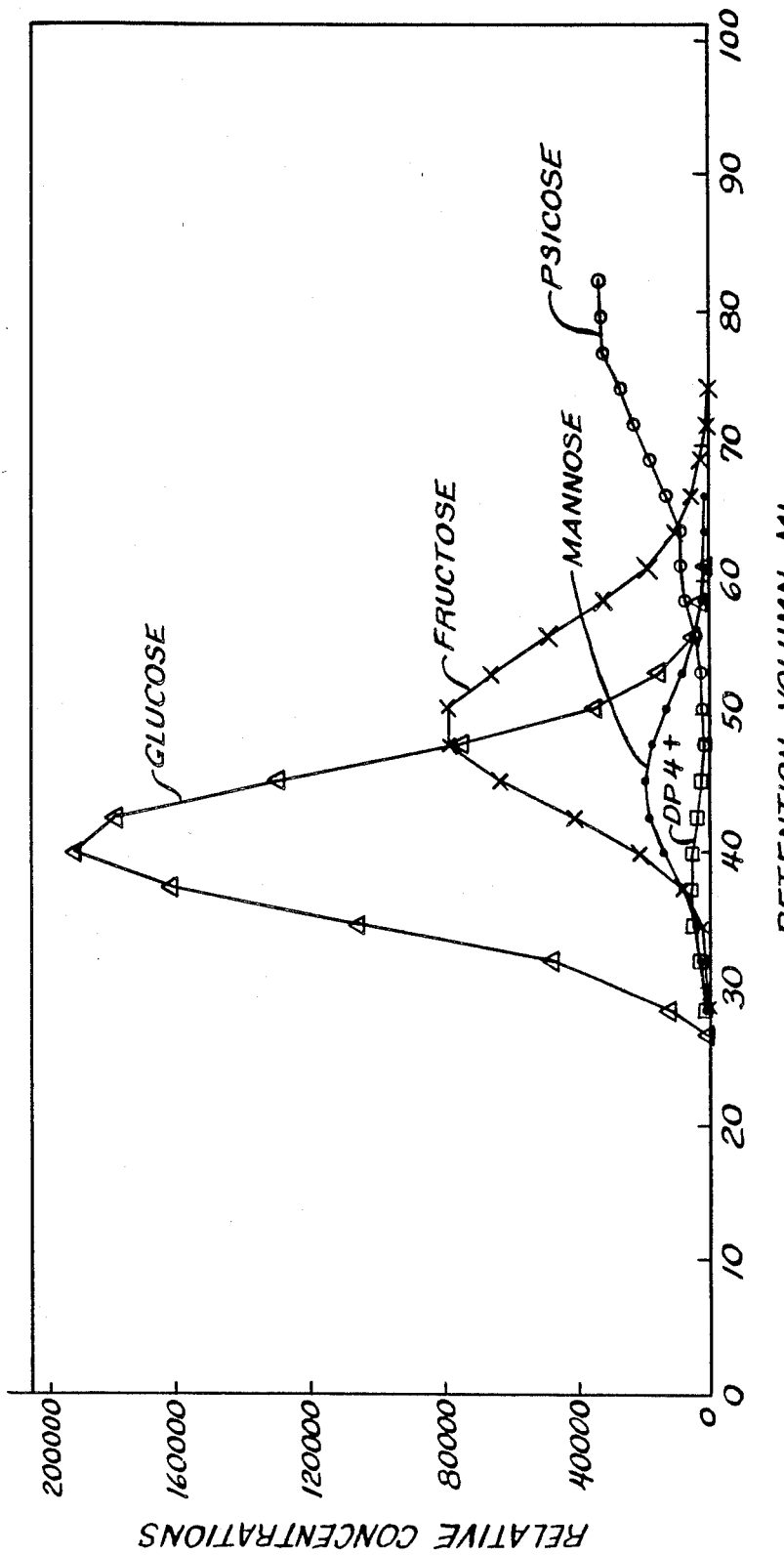

United States Patent [19]

Chang

[11] Patent Number: 4,880,920

[45] Date of Patent: * Nov. 14, 1989

[54] PROCESS FOR SEPARATING KETOSES FROM ALKALINE-OR PYRIDINE-CATALYZED ISOMERIZATION PRODUCTS

[75] Inventor: Chin-Hsiung Chang, Des Plaines, Ill.

[73] Assignee: UOP, Des Plaines, Ill.

[*] Notice: The portion of the term of this patent subsequent to Sep. 8, 2004 has been disclaimed.

[21] Appl. No.: 93,332

[22] Filed: Sep. 4, 1987

Related U.S. Application Data

[63] Continuation-in-part of Ser. No. 811,588, Dec. 20, 1985, Pat. No. 4,692,415.

[51] Int. Cl.$^4$ .............................................. C07H 1/00
[52] U.S. Cl. .................................. 536/127; 536/124
[58] Field of Search ........................ 536/124, 125, 127

[56] References Cited

U.S. PATENT DOCUMENTS

| | | | |
|---|---|---|---|
| 4,014,711 | 3/1977 | Odawara et al. | 536/124 |
| 4,024,331 | 5/1977 | Neuzil et al. | 536/1.1 |
| 4,096,036 | 6/1978 | Liu et al. | 195/31 F |
| 4,226,977 | 10/1980 | Neuzil et al. | 536/127 |
| 4,287,001 | 9/1981 | Kulprathipanja et al. | 536/127 |
| 4,340,724 | 7/1982 | Neuzil et al. | 536/127 |
| 4,345,946 | 8/1982 | Tu et al. | 536/127 |
| 4,358,322 | 11/1982 | Neuzil et al. | 536/1.1 |
| 4,442,285 | 4/1984 | Neuzil et al. | 536/127 |
| 4,471,114 | 9/1984 | Sherman et al. | 536/127 |
| 4,692,514 | 9/1987 | Chang | 536/127 |

FOREIGN PATENT DOCUMENTS 1540556 12/1977 United Kingdom .

OTHER PUBLICATIONS

"Chemistry of the Carbohydrates" by William Ward Pigman and Rudolph Maximilian Goepp, Jr., 1948 Academic Press Inc., Publishers, pp. 41, 126, 127.

*Primary Examiner*—Ronald W. Griffin
*Assistant Examiner*—Nancy S. Carson
*Attorney, Agent, or Firm*—Thomas K. McBride; John F. Spears, Jr.; Jack H. Hall

[57] ABSTRACT

A process for the liquid phase adsorptive separation of psicose from an aqueous feed mixture of monosaccharides containing psicose along with other aldoses and ketoses. The feed is contacted with a calcium-Y type zeolite in two stages. Psicose and fructose are selectively adsorbed to the substantial exclusion of other aldoses and ketoses. In a first embodiment, the extract from the first stage is psicose and fructose is eluted with the raffinate components. In a second embodiment, psicose is again recovered in high purity from the first place as a first extract material while a second extract material, comprising highly purified fructose, is also recovered. The process can be carried out on a commercial scale by means of a simulated moving bed flow scheme.

7 Claims, 1 Drawing Sheet

4,880,920

PROCESS FOR SEPARATING KETOSES FROM ALKALINE- OR PYRIDINE-CATALYZED ISOMERIZATION PRODUCTS

RELATED APPLICATION

This is a continuation-in-part of copending application Ser. No. 811,588, filed December 20, 1985, now U.S. Pat. No. 4,692,514.

BACKGROUND OF THE INVENTION

1. Field of the Invention

The field of art to which this invention pertains is the solid bed adsorptive separation of a ketose from other ketoses and aldoses. More specifically, the invention relates to a process for separating psicose from a mixture comprising psicose, fructose and one or more additional ketoses, and/or aldoses which process employs an adsorbent comprising a calcium-exchanged Y-type zeolite to selectively adsorb psicose from the feed mixture.

2. Information Disclosure

The use of crystalline aluminosilicates in non-hydrocarbon separations is known, e.g., to separate specific monosaccharides or classes of monosaccharides from carbohydrate feed mixtures. A specific example of a class separation is given in U.S. Pat. No. 4,024,331 disclosing the separation of ketoses from a mixture of ketoses and aldoses using a type X zeolite. Specific monosaccharides such as glucose and fructose are isolated from a feed mixture containing the same by an adsorptive separation process using an X zeolite as taught in U.S. Pat. No. 4,442,285.

This invention is particularly concerned with the separation of a ketose, psicose, from another ketose, fructose, mixed with the aldoses, mannose and glucose. Heretofore, no feasible method for commercially separating psicose from the other products of isomerization of aldose sugars, e.g., glucose, was available. Therefore, enzymatic means rather than simple isomerization methods have been used for the production of fructose, because the enzymatic route minimizes the production of psicose. Now, with my discovery of a means for separating psicose from fructose, and other ketoses and aldoses, the simpler, less costly isomerization methods can be used to produce psicose-free fructose. There are two isomerization routes known for obtaining fructose from glucose, namely by the reaction of weak alkali on glucose and the reaction of hot pyridine on glucose. *Chemistry of the Carbohydrates* Pigman et al Academic Press Inc. NY, NY 1948, pages 41, 126–7. Similarly, isomerization of galactose by either of the isomerization techniques referred to above will produce a mixture of aldoses, talose and galactose and a mixture of ketoses, sorbose and tagatose and may be separated by means here disclosed. Furthermore, there is considerable interest in the various L-sugars, which are believed to be low in calories and possibly non-metabolized, which cannot be made enzymatically, but only by isomerization routes such as those mentioned above. This invention applies to the L-sugars as well as D-sugars, and is seen to be an advantageous method for obtaining L-fructose, free of contamination by L-psicose, as well as purified L-psicose.

Data related to potential adsorbents for the separation of mannose from other monosaccharides is set forth in U.S. Pat. No. 4,471,114. This patent contains data related to the use of a Y type faujasite exchanged with calcium cations as an adsorbent for the separation of mannose from glucose and other monosaccharides.

The separation of mannose from glucose is the subject of British Pat. No. 1,540,556. There the adsorbent is a cation exchange resin in salt form, preferably calcium form.

Neuzil et al U.S. Pat. No. 4,340,724 teaches the separation by adsorption of a ketose from an aldose with a Y zeolite exchanged with $NH_4$, Na, K, Ca, Sr, Ba and combinations at the ion exchangeable sites or an X zeolite exchanged with Ba, Na or Sr and combinations thereof.

The separation of psicose from other ketoses is stated in U.S. Pat. No. 4,096,036 to be possible with ion exchange resins capable of complexing with a polyol at a first temperature and dissociating the complex at a second temperature in a thermal parametric pumping apparatus.

SUMMARY OF THE INVENTION

It is accordingly an objective of the present invention to provide a process for the separation of a ketose from a feed mixture which is the alkaline- or pyridine-catalyzed isomerization product of an aldohexose or aldopentose using a Y type zeolite with calcium cations at cation exchanged sites.

The present invention is a process for separating a ketose from a feed mixture comprising the ketose and at least one other monosaccharide selected from the group consisting of ketopentoses and ketohexoses. More specifically, the process comprises contacting at adsorption conditions a monosaccharide comprising a mixture of psicose, fructose and one or more monosaccharides with an adsorbent comprising a type Y zeolite containing calcium cations at the exchangeable cationic sites, selectively adsorbing psicose preferentially to the fructose and to the substantial exclusion of the other monosaccharides, removing the nonadsorbed portion of the feed mixture from contact with the adsorbent, and thereafter recovering the psicose by desorption at desorption conditions as a single extract containing only psicose or as two extracts in which psicose and fructose are recovered as separate extracts. In the first case, fructose will be collected with the other raffinate materials. In the latter case, fructose may be further processed to obtain highly purified fructose as a product in addition to psicose. Psicose can be further purified by contacting the psicose extract with a second bed of Y-type zeolite exchanged by calcium at the exchangeable sites, selectively and preferentially adsorbing the psicose and recovering the psicose in the extract by desorption at desorption conditions with water as desorbent. This process is especially useful and attractive for the separation and recovery of L-psicose and/or L-fructose from catalytic isomerization mixtures of L-sugars.

Other objectives and embodiments of the present invention relate to specific feed mixtures, adsorbents, desorbent materials, operating conditions and flow configurations, all of which are hereinafter disclosed in the following discussion of the present invention.

DESCRIPTION OF THE INVENTION

At the outset the definitions of various terms used through the specification will be useful in making clear the operation, objects and advantages of this process.

A "feed mixture" is a mixture containing one or more extract components and one or more raffinate components to be separated by this process. The term "feed stream" indicates a stream of a feed mixture which passes to the adsorbent used in the process.

An "extract component" is a component that is more selectively adsorbed by the adsorbent while a "raffinate component" is a component that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary. from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream, and preferably at least a portion of the raffinate stream, from the separation process are passed to separation means, typically fractionators or evaporators, where at least a portion of desorbent material is separated to produce an extract product and a raffinate product. The term "extract product" and "raffinate product" mean products produced by the process containing, respectively, an extract component and a raffinate component in higher concentrations than those found in the extract stream and the raffinate stream.

The adsorbent materials of this invention comprise type Y crystalline aluminosilicates having calcium cations at cation exchange sites. The type Y crystalline aluminosilicates or zeolites can be further classified as faujasites. As in the general case of all zeolites, these crystalline compounds are described as a threedimensional network of fundamental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension. Zeolites are more fully described and defined in U.S. Pat. Nos. 2,883,244 and 3,130,007 respectively, incorporated herein by reference thereto. The Y zeolites in the hydrated or partially hydrated form can be represented in terms of mole oxides as shown in Formula 1 below, in which "M" is a cation having a valence up to 3, "n" is the valence of "M", "w" is a value from 3 to 6 and "y" is a value up to 9, depending on the identity of "M" and the degree of hydration of the crystal:

Formula 1

$(0.9 \pm 0.2)M_{2/n}O:Al_2O_3:wSiO_2:yH_2O$

The electrovalence of the tetrahedra is balanced by the cation "M" of the above equation which occupies exchangeable cationic sites in the zeolite. These cations which after initial preparation are predominantly sodium may be replaced with other cations by ion exchange methods well known to those having ordinary. skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes places, the sieves are removed from the aqueous solution, washed and dried to a desired water content. By such methods, the sodium cations and any nonsodium cations which might be occupying exchangeable sites as impurities in a sodium-Y zeolite can be partially or essentially completely replaced with other cations. It is essential that the zeolite used in the process of my invention contains calcium cations at exchangeable cationic sites.

Typically, adsorbents used in separative processes contain zeolite crystals and amorphous material. The zeolite will typically be present in the adsorbent in amounts ranging from about 75 wt. % to about 98 wt. % based on volatile free composition. The remainder of the adsorbent will generally be amorphous material such as silica, or silica-alumina mixtures or compounds, such as clays, which material is present in intimate mixture with the small particles of the zeolite material. This amorphous material may be an adjunct of the manufacturing process for zeolite (for example, intentionally incomplete purification of either zeolite during its manufacture), or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The adsorbent used in our process will preferably have a particle size range of about 16-40 mesh (Standard U.S. Mesh). I have found that Y zeolite with calcium cations and amorphous binders possess the selectivity and other necessary requirements previously discussed and is therefore suitable for use in my process.

Certain carbohydrates or so-called simple sugars are classified as monosaccharides. These monosaccharides are hydroxyaldehydes or hydroxyketones containing one ketone or aldehyde unit per molecule and two or more alcohol functionalities. Thus monosaccharides are classified as aldoses or ketoses on the basis of their carbonyl unit. Ketoses and aldoses are further classified by their carbon skeleton length. Accordingly, five-carbon and six-carbon monosaccharides receive the respective names of pentoses and hexoses. Well-known aldohexoses include glucose, mannose and galactose. Arabinose, ribose and xylose are well-known aldopentoses. Examples of common ketohexoses are fructose, psicose and sorbose. Ribulose and xylulose are common ketopentoses. This invention is a process for eparating psicose from feed mixtures containing other ketopentoses and ketohexoses as referred to above.

Consequently, feed mixtures which can be utilized in the process of this invention will comprise a mixture of psicose and at least one other ketose. Potential feed mixtures can be found in isomerization products of D-glucose and L-glucose. Such mixtures will usually contain significant quantities of such monosaccharides as psicose, fructose, glucose, mannose and small quantities of polysaccharides, such as DP 4+, i.e. having a degree of polymerization of four and greater. The feed mixtures whether derived from natural sources or isomerization, will also contain quantities of lesser known monosaccharides. A typical feed mixture for this invention will contain psicose, fructose, mannose, glucose and polysaccharides in respective proportions, based on weight percent of solids, ranging from 0.5 to 90 wt. %. In addition, there may be up to 10 wt. % solids of other lesser known sugars.

Although it is not clear what properties of the adsorbent are responsible for the separation herein described, it appears that it cannot be attributed to pore size selectivity alone. Since psicose and fructose are separated from sugar molecules of similar size, it appears that steric factors as well as electrostatic attraction action play an important role in the separation. While it is not possible to conclusively set forth the molecular interaction responsible for the adsorption, one possible explanation is a combination of cation attraction which varies the orientation of specific sugar molecules to the pore opening on the adsorbent. This varied orientation can provide a suitable disposition of the particular structural configuration corresponding to certain sugar molecules which coincides with the shape of the adsorbent pore openings as altered by the presence of specific cations. Therefore, both electrostatic interaction as well as physical and stoichiochemical considerations may provide the mechanism for this separation.

Although it is possible by the process of this invention to produce high purity products, it will be appreciated that an extract component is never completely adsorbed by the adsorbent, nor is a raffinate component completely unadsorbed by the adsorbent. Therefore, small amounts of a raffinate component can appear in the extract stream, and likewise, small amounts of an extract component can appear in the raffinate stream. The extract and raffinate stream then are further distinguished from each other and from the feed mixture by the ratio of the concentrations of an extract component and a specific raffinate component, both appearing in the particular stream. For example, the ratio of concentration of the more selectively adsorbed to the concentration of less selectively adsorbed sugars will be highest in the extract stream, next highest in the feed mixture, and lowest in the raffinate stream. Likewise, the ratio of the less selectively adsorbed sugars to the more selectively adsorbed will be highest in the raffinate stream, next highest in the feed mixture, and the lowest in the extract stream.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent material must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent material, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but othersseparation methods such as reverse osmosis may also be employed alone or in combination with distillation or evaporation. Since the raffinate and extract products are foodstuffs intended for human consumption, desorbent material should also be nontoxic. Finally, desorbent materials should also be materials which are readily available and therefore reasonable in cost. Suitable desorbents for this separation comprise water and ethanol or mixtures thereof.

The prior art has recognized that certain characteristics of adsorbents and desorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent.

Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, for one component as compared to another component. Relative selectivity can be expressed not only for one feed component as compared to another, but can also be expressed between any feed mixture component and the desorbent material. The selectivity, (B), is defined as the ratio of the two components of the adsorbed phase divided by the ratio of the same two components in the unadsorbed phase at equilibrium conditions, as shown in Equation 1, below:

Equation 1
$$\text{Selectivity} = (B) = \frac{[\text{wt. percent } C/\text{wt. percent } D]_A}{[\text{wt. percent } C/\text{wt. percent } D]_U}$$

where C and D are two components of the feed represented in weight percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases. Where selectivity of the adsorbent for two components approaches 1.0, there is no preferential adsorption of one component by the adsorbent with respect to the other; they are both adsorbed (or nonadsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible whentthe selectivity of the adsorbent for the extract component with respect to the raffinate component is just slightly greater than 1.0, it is preferred that such selectivity be reasonably greater than 1.0. Like relative volatility, the higher the selectivity. the easier the separation is to perform. Higher selectivities permit a smaller amount of adsorbent to be used.

The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The adsorption-desorption operations may be carried out in a dense fixed bed which is alternatively contacted with a feed mixture and a desorbent material in which case the process will be only semicontinuous. In another embodiment, generally referred to as a swing bed system, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Countercurrent moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continuous use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of adsorbent contained in the chamber.

Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of this process, it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be in a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone, or zone 3. The desorption zone is defined as the adsorbent between the desorbent inlet and the extract outlet streams. The function of the desorption zone is to allow a desorbent material which passes into this zone to displace the contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3, thereby contaminating the extract stream removed from zone 3. In the instances in which the fourth operational zone is not utilized, the raffinate stream passing from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams, thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent, that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternatively and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated under separating conditions to produce a desorbent stream which can be reused in the process and a raffinate product containing a reduced concentration of desorbent material. The separation means will typically be a fractionation column or an evaporator, the design and operation of either being well-known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on April 2, 1969 (both of which are incorporated herein by reference), for further explanation of the simulated moving bed countercurrent process flow scheme.

Although both liquid and vapor phase operations can be used in many adsorptive separation processes, liquid-phase operation is required for this process because of the lower temperature requirements and because of the higher yields of extract product that can be obtained with liquid-phase operation over those obtained with vapor phase operation. Adsorption conditions will include a temperature range of from about 20° C. to about 200° C. with about 20° C. to about 100° C. being preferred and a pressure range of from about atmospheric to about 500 psig with from about atmospheric to whatever pressure is required to ensure liquid phase being preferred. Desorption conditions will include the same range of temperatures and pressures as used for adsorption conditions.

The size of the units which can utilize the process of this invention can vary anywhere from those of pilot plant scale (see for example U.S. Pat. No. 3,706,812 to de Rosset et al) to those of commercial scale and can range in flow rates from as little as a few cc an hour up to many thousands of gallons per hour.

Another embodiment of a simulated moving bed flow system suitable for use in the process of the present invention is the cocurrent high efficiency. simulated moving bed process disclosed in U.S. Pat. No. 4,402,832 to Gerhold, incorporated by reference herein in its entirety.

A dynamic testing apparatus may be employed to test various adsorbents with a particular feed mixture and desorbent material to measure the adsorbent characteristics of adsorptive capacity, selectivity. and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed polysaccharide tracer maltrin-$DP_{4+}$, aldoses, and other trace sugars, all diluted in desorbent, is injected for a duration of several minutes. Desorbent flow is resumed, and the tracer and the aldoses are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

The pulse test run in Example I of the parent case using a Y type zeolite having $Ca^{++}$ ions at cation exchange sites showed the separation of psicose from carbohydrate mixtures containing the same. The calcium exchanged Y type zeolite of the example bound in an organic binder was packed in a 8.4 mm diameter column having a total volume of 70 cc.

FIG. 1 provides a graphical representation of the adsorbent's relative strength of the retention of the psicose, fructose and other sugars.

A consideration of the average midpoint for each concentration curve reveals a good separation of psicose from the other feed mixture components. Psicose is clearly the most selectively, or strongly, retained component. Moreover, fructose is also selectively retained from among the remaining components, and may be separated from nonadsorbed components and the more strongly adsorbed psicose by the Ca-Y adsorbent in the same or a different adsorbent bed. From the data obtained from this experiment the selectivities of Table 1 were calculated.

TABLE 1

| Selectivity (B) | |
| --- | --- |
| Psicose/Fructose | 3.76 |
| Fructose/Mannose | 1.68 |
| Fructose/Glucose | 4.84 |

These selectivities clearly establish the achievement of a high degree of separation for psicose and also a satisfactory separate recovery of fructose from the remaining components of the feed in a second extract in the first stage. According to the present invention, the psicose may be further purified in a second stage by passing the first extract over the same Ca-Y adsorbent column or another Ca-Y bed, e.g., elution column.

The examples shown below are intended to further illustrate the process of this invention and is not to be construed as unduly limiting the scope and spirit of said process.

EXAMPLE I

An aqueous feed, as described below in Table 2, was contacted, in a countercurrent flow, simulated moving bed system described above with a calcium-exchanged Y zeolite adsorbent, which was desorbed with water. The valve cycle was 1 hour, the temperature was 65° C. and the ratio of adsorbent to feed, A/F, was 0.9. The feed was obtained by the isomerization of L-glucose at 37° C. and a pH of 10.6 for 48 hours.

TABLE 2

| Feed | Wt. & Dry Solids |
| --- | --- |
| L-Glucose | 51.0 |
| L-Fructose | 28.7 |
| L-Mannose | 7.7 |
| L-Psicose | 5.3 |
| Unknown | 3.4 |
| $DP_2$ | 1.8 |
| $DP_3$ | 1.4 |
| $DP_4+$ | 0.5 |

In the first stage, most of the fructose was recovered in the extract stream and thus separated from the remaining feed components, as will be seen from the product analysis in Table 3 below, under conditions to optimize fructose recovery free of psicose contamination. The extract from the first stage, consisting of highly pure L-fructose and a reduced concentration of L-psicose was then treated in a column containing calcium-exchanged Y faujasite. The L-psicose, being more strongly adsorbed by the zeolite, was found greatly purified, in this final extract stream while most of the L-fructose was obtained, substantially free of L-psicose (0.5%), in the raffinate stream, with minor amounts of other components, at a purity of 94.1%. L-psicose can be recovered in still greater concentration in the second extract by optimizing the first stage with respect to psicose recovery as will be shown in Example II. An analysis of the combined raffinate of two consecutive periods of the separation run show the composition of the raffinate to be high in L-fructose with small amounts of L-psicose and other components of the feed mixture.

TABLE 3

| Component | Sorbex/w/Ca—Y First Stage Extract (Feed to 2nd Stage) | Ca—Y Elution Column Second Stage Final Extract | Ca—Y Elution Column Second Stage Final Raffinate |
|---|---|---|---|
| DP$_4$+ | 0.05 | 0.1 | — |
| DP$_3$ | — | — | — |
| DP$_2$ | 0.1 | 0.3 | — |
| L-Frutose | 91.8 | 83.2 | 94.1 |
| L-Glucose | 0.4 | 1.1 | 1.0 |
| L-Mannose | 2.8 | 4.6 | 2.2 |
| L-Psicose | 2.0 | 6.0 | 0.5 |
| Others | 2.8 | 4.6 | 2.2 |

EXAMPLE II

An aqueous feed, as described below in Table 4, was separated in a countercurrent flow, simulated moving bed system described above in which the adsorbent was a calcium-exchanged Y zeolite and the desorbent was water. The valve cycle was 1 hour, the temperature was 65° C. and the ratio of adsorbent to feed, A/F, was 1.15. The feed was obtained by the isomerization of glucose at 37° C. and a pH of 10.6 for, 48 hours.

TABLE 4

| Feed | Wt. % Dry Solids |
|---|---|
| Glucose | 55.4 |
| Fructose | 29.2 |
| Mannose | 6.1 |
| Psicose | 5.6 |
| Others, including DP$_2$, DP$_3$, DP$_4$ and unknown | 3.7 |
| Total | 100 |

In the first stage, most of the fructose and psicose were separated from the remaining components in the extract stream, as will be seen from the product analysis in Table 5, below. The extract from the first stage, enriched in psicose may then be treated in an elution column containing calcium-exchanged Y faujasite. The psicose, being more strongly adsorbed by the zeolite, will be greatly purified in the final extract stream, while most of fructose was obtained, substantially free of psicose (0.5%), in the raffinate stream, with minor amounts of other components, at purity of at least 90%. First extract composition data from four first-stage runs (feed to the second stage separation), and the composition of the raffinate of Run No. 1 only are shown in Table 5.

TABLE 5

| | First Stage Separation | | | | |
|---|---|---|---|---|---|
| | First Raffinate | First Extract | | | |
| Component | Run #1 | Run #1 | Run #2 | Run #3 | Run #4 |
| L-Fructose | 22.7 | 82.6 | 82.8 | 83.3 | 84.4 |
| L-Glucose | 66.8 | .8 | — | — | — |
| L-Mannose | 6.7 | 2.9 | 2.7 | 3.3 | 3.8 |
| L-Psicose | 0.35 | 7.8 | 10.5 | 8.3 | 7.9 |
| Other, incl. DP$_2$ | — | 5.9 | 3.6 | 5.1 | 3.9 |

Using first stage extract recovery data from Example I (Example 111 of the parent case), recovery. of the components were calculated for a second-stage separation of the first stage extracts of the above runs by elution in a Ca-Y zeolite packed column. The calculated results, to maximize recovery of both fructose and psicose, are set forth in the following table.

TABLE 6

| | Theoretical Distributions After 2nd Stage (Ca—Y Elution Column) | | | |
|---|---|---|---|---|
| Component | Raffinate | Extract | Raffinate | Extract |
| | Run #1 | | Run #2 | |
| Glucose | 0.2 | 2.1 | — | — |
| Fructose | 90.3 | 65.3 | 91.9 | 64.3 |
| Mannose | 2.4 | 4.1 | 2.2 | 3.7 |
| Psicose | 2.2 | 20.3 | 2.9 | 27.0 |
| Other | 4.9 | 8.3 | 2.9 | 5.0 |
| Total | 100.0 | 100.0 | 99.9 | 100.0 |
| | Run #3 | | Run #4 | |
| Glucose | — | −1 | — | — |
| Fructose | 90.8 | 66.3 | 91.4 | 68.2 |
| Mannose | 2.7 | 4.6 | 3.2 | 5.3 |
| Psicose | 2.3 | 21.9 | 2.1 | 21.2 |
| Other | 4.2 | 7.2 | 3.3 | 5.3 |
| Total | 100.0 | 100.0 | 100.0 | 100.0 |

Further extrapolations can be made based on the theoretical separations possible with the selectivities exhibited by the present adsorbent (Table 1) in order to obtain very. high purity psicose (with correspondingly low recoveries) by recovering in, or limiting, the second stage extract, to only that portion of the retention volume curve represented in FIG. 1 greater than about 70 ml; psicose purity, up to about 99% is possible with estimated recoveries of 10% to 20% Psicose purities of 20 to 50% are prefered to obtain a sufficiently high percent recovery for economic justification.

I claim:

1. A process for recovering psicose having a purity of 20–99% (wt.) from a feed mixture comprising fructose and psicose and at least on Ⓡ other monosaccharide selected from the group consisting of glucose and mannose which comprises contacting at adsorption conditions said feed mixture with a adsorbent comprising a type Y zeolite having calcium cations at exchangeable sites, selectivley adsorbing said psicose preferentiallhy to said fructose and to the substantial exclusion of the other components, recovering an extract mixture comprising enriched psicose and fructose and then contacting said extract mixture with an adsorbent comprising a type Y zeolite having calcium cations at exchangeable sites, selectively adsorbing said psicose and recovering highly purified psicose by desorption at desorption conditions.

2. The process of claim 1 wherein said mixture comprises L-psicose, L-fructose, L-glucose and L-mannose.

3. The process of claim 1 wherein said desorbent comprises water.

4. The process of claim 1 wherein said separation is effected by means of a simulated moving bed flow scheme.

5. The process of claim 4 wherein said simulated moving bed scheme uses countercurrent flow.

6. The process of claim 1 wherein said simulated moving bed scheme uses cocurrent flow.

7. The process of claim 1 wherein a second extract, comprising fructose, is recovered from said step of contacting said feed mixture.

* * * * *

UNITED STATES PATENT AND TRADEMARK OFFICE
CERTIFICATE OF CORRECTION

PATENT NO.   : 4,880,920
DATED        : November 14, 1989
INVENTOR(S)  : Chang

It is certified that error appears in the above-identified patent and that said Letters Patent is hereby corrected as shown below:

In Column 14, line 37: Change "on®" to --one--;

line 42: Change "selectivley" to --selectively--.

Signed and Sealed this

Twenty-second Day of January, 1991

Attest:

HARRY F. MANBECK, JR.

*Attesting Officer*    *Commissioner of Patents and Trademarks*